United States Patent
Chen

(10) Patent No.: US 9,715,023 B2
(45) Date of Patent: Jul. 25, 2017

(54) DETECTOR IN AN IMAGING SYSTEM

(71) Applicant: SHANGHAI UNITED IMAGING HEALTHCARE CO., LTD., Shanghai (CN)

(72) Inventor: Ze Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 15/198,274

(22) Filed: Jun. 30, 2016

(65) Prior Publication Data

US 2017/0146672 A1    May 25, 2017

(30) Foreign Application Priority Data

Nov. 19, 2015  (CN) .......................... 2015 1 0801821

(51) Int. Cl.
| | |
|---|---|
| *G01T 1/20* | (2006.01) |
| *G01T 1/29* | (2006.01) |
| *G01T 7/00* | (2006.01) |
| *G01T 1/208* | (2006.01) |

(52) U.S. Cl.
CPC .............. *G01T 7/005* (2013.01); *G01T 1/208* (2013.01); *G01T 1/2018* (2013.01); *G01T 1/2985* (2013.01)

(58) Field of Classification Search
CPC ..... G01T 1/2018; G01T 1/208; G01T 1/2985; G01T 7/005
See application file for complete search history.

(56) References Cited

U.S. PATENT DOCUMENTS

| | | | | |
|---|---|---|---|---|
| 4,972,077 | A | * | 11/1990 | Willson ................ G01D 5/268 250/205 |
| 5,444,280 | A | * | 8/1995 | Blouke ................ H01L 31/107 257/226 |
| 5,504,386 | A | | 4/1996 | Kyushima et al. |
| 6,222,192 | B1 | | 4/2001 | Sekela et al. |
| 6,287,128 | B1 | | 9/2001 | Jones et al. |
| 7,512,210 | B2 | | 3/2009 | Possin et al. |
| 7,633,057 | B2 | | 12/2009 | Cooke et al. |
| 8,222,607 | B2 | | 7/2012 | Mann |
| 8,415,631 | B2 | | 4/2013 | Moriyasu et al. |
| 8,859,951 | B2 | | 10/2014 | Wang et al. |
| 8,907,290 | B2 | | 12/2014 | Kim et al. |
| 9,489,735 | B1 | * | 11/2016 | Reitmayr ............. G06T 7/0018 |

(Continued)

FOREIGN PATENT DOCUMENTS

| | | |
|---|---|---|
| CN | 101071705 A | 11/2007 |
| CN | 102328166 B | 1/2012 |

(Continued)

OTHER PUBLICATIONS

International Search Report for PCT/CN2016/105295 mailed on Feb. 17, 2017, 5 pages.

(Continued)

*Primary Examiner* — Mark R Gaworecki
(74) *Attorney, Agent, or Firm* — Metis IP LLC

(57) ABSTRACT

The disclosure relates to a system and method for evaluating and calibrating detector in a scanner, further evaluating and calibrating time information detected by at least one time-to-digital convertor.

15 Claims, 19 Drawing Sheets

(56) References Cited

U.S. PATENT DOCUMENTS

| | | | |
|---|---|---|---|
| 2006/0091285 A1* | 5/2006 | Warner | G01J 1/32 |
| | | | 250/205 |
| 2008/0203309 A1* | 8/2008 | Frach | G01T 1/1642 |
| | | | 250/362 |
| 2010/0134335 A1 | 6/2010 | Park et al. | |
| 2010/0155610 A1* | 6/2010 | Menge | G01T 1/00 |
| | | | 250/368 |
| 2011/0155899 A1* | 6/2011 | Dror | G01T 1/171 |
| | | | 250/252.1 |
| 2011/0227621 A1 | 9/2011 | Ridgers | |
| 2012/0163556 A1* | 6/2012 | Henning | A61N 5/1049 |
| | | | 378/198 |
| 2013/0307713 A1 | 11/2013 | Kawaguchi et al. | |
| 2015/0276953 A1* | 10/2015 | Espana Palomares | G01T 1/1648 |
| | | | 702/104 |

FOREIGN PATENT DOCUMENTS

| | | |
|---|---|---|
| CN | 104111468 A | 10/2014 |
| CN | 104337531 A | 2/2015 |
| CN | 104352244 A | 2/2015 |

OTHER PUBLICATIONS

Written Opinion for PCT/CN2016/105295 mailed on Feb. 17, 2017, 4 pages.

\* cited by examiner

DETECTOR IN AN IMAGING SYSTEM

CROSS-REFERENCE TO RELATED APPLICATIONS

This application claims priority of Chinese Patent Application No. 201510801821.X filed on Nov. 19, 2015, the contents of which are hereby incorporated by reference.

TECHNICAL FIELD

This present disclosure relates to imaging device, and more particularly, relates to a system and method for evaluating and calibrating the imaging device in data detecting and processing.

BACKGROUND

Positron emission tomography (PET) has been widely used in medicine for diagnosis and other purposes. An object, such as a patient, may be scanned with a PET system to obtain PET datasets. Precise image reconstruction may be based on precise datasets reflecting the actual condition. Precise datasets may depend on the detector and data processing module in a good working condition. Method for evaluating and calibrating the photodetector and time information have been developed.

Generally, in medical imaging, consistency of the scanners is of great importance. One of the most significant challenges in maintaining the stability of a scanner in nuclear imaging is keeping a photodetector in a precise working condition. Output of a photodetector is known to drift over time, as a result of usage and temperature. For technicians, an evaluation of the photodetector before or during the detecting may be necessary, traditional calibration method may introduce extraneous radiation source.

Datasets may be processed after the detecting procedure of the photodetector. Time information of each electrical signal may be extracted precisely during the data processing. However, due to the nonlinearity of the delay-line, the time information may be sometimes calculated erroneously. Thus, a calibration during the extraction of time information may be indispensable.

SUMMARY

This application relates generally to evaluation or calibration of photodetector and time information. A method and related system disclosed herein can provide a more precise image.

One aspect of the present disclosure relates to a method for evaluating or calibrating a working condition of a photodetector in an imaging device. The method may include receiving radiation by a photodetector; generating an electronic signal relating to a plurality of single events by the photodetector in response to the received radiation; determining a parameter relating to the plurality of single events; and evaluating the working condition of the photodetector based on the parameter and a threshold.

In one example, the parameter may be a single event count or a characteristic of a photon energy spectrum of the electrical signal detected by the photodetector. In some embodiments, the corresponding working condition may be that the single event count of the photodetector is within a range determined by a threshold. In some other embodiments, the parameter may be a characteristic of a photon energy spectrum and the corresponding working condition may be that the deviation of the peak position from the characteristic radiation peak does not exceed a threshold. The method may further include determining the position of a first peak of the photon energy spectrum; determining the position of a characteristic peak corresponding to the first peak; determining a deviation between the position of the first peak and the position of the characteristic peak; and assigning the photodetector into the first set if the deviation is below the threshold.

In a further example, the electronic signal may comprise time related information processed by a time-to-digital convertor (TDC). In some embodiments, the calibration method of TDC channels may include obtaining single events distribution of multiple TDC channels; selecting a reference channel, wherein the selected reference channel may divide the multiple TDC channels into different sets of TDC channels based on the reference channel such that the number of single events of one set is equal to the number of single events of another set; setting a reference time to the reference channel, wherein the reference time is prefer to be set as half of a clock period of the TDC; calculating a time value of a characteristic channel based on the reference time; and as a result of iteration, time of all the other TDC channels may be calculated. In some embodiments, one set of TDC channels may be on left side of the reference channel in a column diagram, another set of TDC channels may be on right side of the reference channel in the column diagram. The value relating to the characteristic TDC may be calculated based on the reference time, a serial number of the characteristic TDC channel, the single event count of the characteristic TDC channel, and a clock period of the TDC.

Another aspect of the present disclosure relates to a system comprising a detector for receiving radiation in respond to which a plurality of single events occur. The detector may comprise a photodetector of the detector for generating an electronic signal relating to the plurality of single events. The system may further comprise a processing module for determining a parameter of the electronic signal relating to the plurality of single events and evaluating the working condition of the photodetector based on the parameter and a threshold. The threshold may be set by default or may be determined based on the received radiation.

In one example, radiation may be detected by a scintillator. In some embodiments, the radiation may be background radiation of a scintillator containing lutetium and exhibiting at least one characteristic radiation, and the characteristic radiation may be detected by another one or more scintillators. In some embodiments, the radiation may be generated by an extra light source rather than background radiation. In a PET system, the source used for calibrating a photodetector may be a light source such as a LED or light guided by a fiber.

In a further example, the photodetector may be a photomultiplier, a silicon photomultiplier, an avalanche diode or a combination thereof. In some embodiments, the photodetector may be connected with a voltage divider and they may be welded together by a welding device. The photodetector may be calibrated by a circuit or a software if working condition of the photodetector is unsuitable.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
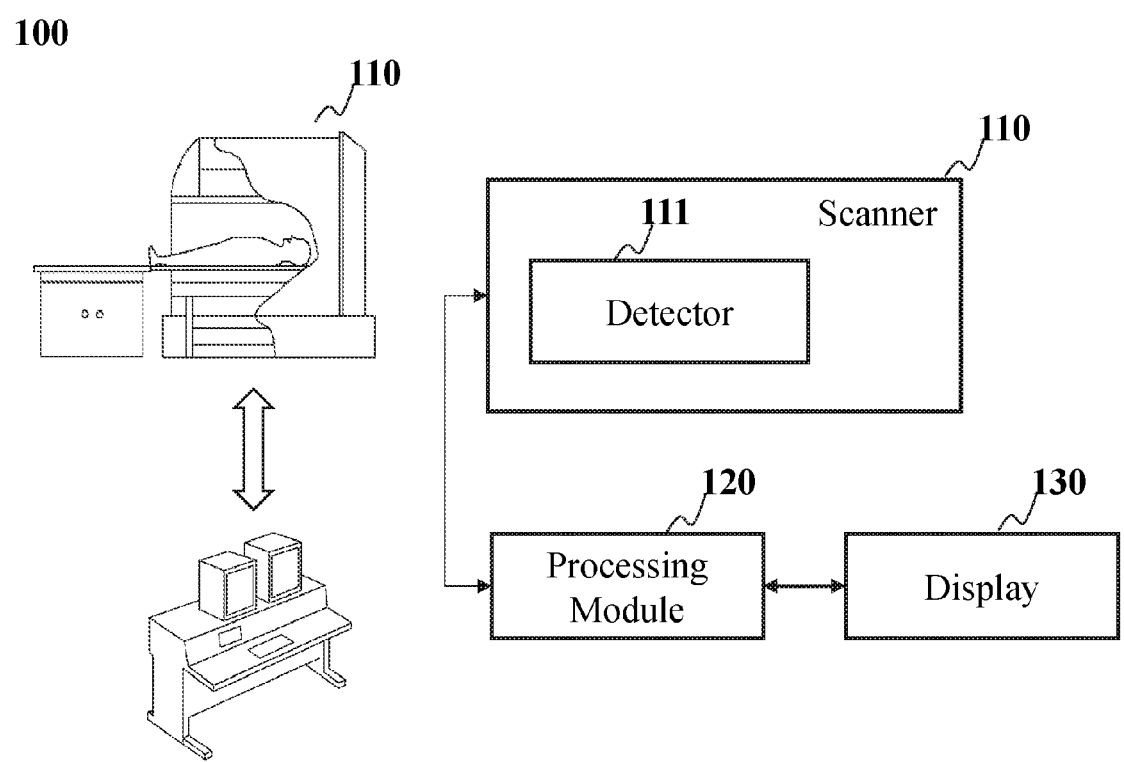
FIG. 1 is a diagram of an imaging system according to some embodiments of the present disclosure.

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "construction" and "reconstruction," when used in this disclosure, may represent a similar process in which an image may be transformed from data. Moreover, the phrase "medical imaging system," "imaging system," and the phrase "diagnostic imaging system" may be used interchangeably. In some embodiments, image system may include data acquisition and image reconstruction, etc.

The present disclosure provided herein relates to an imaging system including, a photodetector and/or a TDC circuit. Specifically, the method may be carried out in the form of circuits. In some embodiments, the method may be achieved by hardware, software, or a combination thereof. The method and system may be used in a calibration process based on photovoltaic conversion and signal processing acquired by, for example, a positron emission tomography (PET) system, a single photon emission computed tomography (SPECT) system, a computed tomography (CT) system, a digital radiography (DR) system, a multi-modality system, a magnetic resonance (MR) imaging system, or the like, or a combination thereof.

FIG. 1 is a block diagram of an imaging system 100 according to some embodiments of the present disclosure. It should be noted that the imaging system 100 described below is merely provided for illustration purposes, and not intended to limit the scope of the present disclosure. The radiation used herein may include a particle ray, a photon ray, or the like, or any combination thereof. The particle ray may include neutron, proton, α-ray, electron, µ-meson, heavy ion, or the like, or any combination thereof. The photon beam may include X-ray, γ-ray, ultraviolet, laser, or the like, or any combination thereof. The radiation may include visible light or invisible light. The imaging system may find its applications in different fields such as, for example, medicine or industry. Merely by way of example, the imaging system may be a positron emission tomography (PET) system, a single photon emission computed tomography (SPECT) system, a computed tomography (CT) system, a digital radiography (DR) system, a multi-modality system, or the like, or any combination thereof. Exemplary multi-modality system may include a computed tomography-positron emission tomography (CT-PET) system, a single photon emission computed tomography-magnetic resonance (SPECT-MR) system, etc. As another example, the system may be used in internal inspection of components including, e.g., flaw detection, security scanning, failure analysis, metrology, assembly analysis, void analysis, wall thickness analysis, or the like, or any combination thereof.

As illustrated in FIG. 1, the imaging system 100 may include a scanner 110, a processing module 120 and a display 130. The scanner 110 may include a detector 111 that may produce an electrical signal relating to a subject to the processing module 120. Merely by way of example, in a PET system, the electric signal may correspond to an event when a photon is detected by a photovoltaic device. The processing module 120 may process the electric signal to reconstruct an image of the subject. Further, the image may be displayed on the display 130. The processing module 120 and the display 130 may take the form of hardware, software, or the combination thereof. In some embodiments, the processing module 120 and the display 130 both may be integrated on circuits in an operative and displaying device. The scanner 110 may include an opening that an object, for example, a patient, may be located for scanning.

Figure 2:
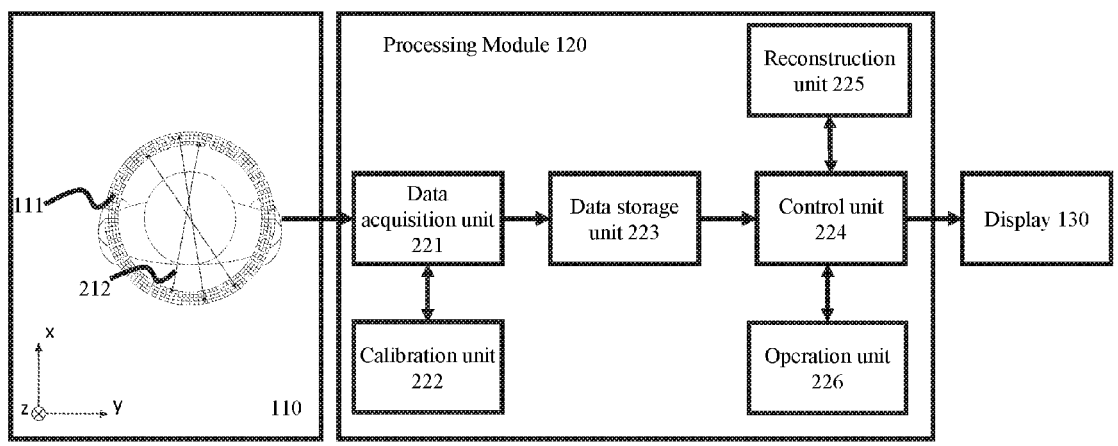
FIG. 2 is a block diagram of an image system according to some embodiments of the present disclosure.

FIG. 2 is a block diagram of the image system according to some embodiments of the present disclosure. For illustration purposes, a PET system is described. It shall be noted that the description herein may also apply to other radiation imaging systems, including but not limit to a CT system, an MR system, a SPECT system, a PET-CT system, etc. The PET scanner 110 may include a detector 111 for detecting lines of response 212.

As shown, the detector 111 may include a plurality of detector cells. The detector cells may be arranged in the form of a ring, a cylinder, a portion thereof, to surround the object being scanned. In some embodiments, the detector 111 may include a plurality of detector rings. The detector rings may form a field of view (FOV). In some embodiments, the detector cells may be placed within the wall of the PET scanner 110. In some embodiments, a detector cell may detect gamma rays. A patient injected with radiopharmaceutical may lie on a bed parallel to the z axis of the PET scanner 110. The radiopharmaceutical includes radioisotopes that may decay and emit gamma rays of characteristic energy. The gamma ray photons may be generated in an electron-positron annihilation event and propagate in opposite directions such that two gamma ray photons travel in opposite directions may be detected by two detector cells.

When the annihilation events occur within the PET scanner 110, they may be detected as a coincidence event if both gamma ray photons strike detector cells substantially simultaneously. In order to validate a coincidence event, the processing module 120 may detect the time information of electrical pulses from the detector 111 when incident gamma ray photons are detected.

As used herein, a line of response (LOR) may be determined by connecting the two detector cells of a coincidence event and the annihilation point may be determined based on the time information of the two single events. It should also be noted here that the "line of response" or "LOR" used here may be representative of a radiation ray, and not intended to limit the scope of the present disclosure. The radiation ray used herein may include a particle ray, a photon ray, or the like, or any combination thereof. The particle ray may include particles such as, a neutron, a proton, an electron, a μ-meson, a heavy ion, or the like, or any combination thereof. For example, the radiation ray may represent the intensity of an X-ray beam passing through the subject in the case of a CT system. As another example, the radiation ray may represent the probability of a positron generated in the case of a PET system.

The processing module 120 may include a data acquisition unit 221, a calibration unit 222, a data storage unit 223, a control unit 224, a reconstruction unit 225 and an operation unit 226. Data from the detector 111 may be received by the data acquisition unit 221 for storing by the data storage unit 223 or subsequent processing by other units. In some embodiments, coincidence events may be stored in the data storage unit 223. In some embodiments, the storage unit 223 may be a random access memory (RAM), a read only memory (ROM), a solid state disk, a compact disk, a combination of the above or a memory with other forms.

In some embodiments, the data may be calibrated by the calibration unit 222 before being reconstructed into an image by the reconstruction unit 225. The reconstruction unit 225 reconstructs the image based on the amplitude and time information of every coincidence event. The control unit 224 may take control the sequence of the image reconstruction process based on parameters by default or instructions acquired at the operation unit 226. The control unit 224 may communicate with the data storage unit 223, the reconstruction unit 225, the operation unit 226 and the displaying module 230 in a wired or wireless manner. The reconstructed image may be transmitted to the display 130 for display.

Further, while not shown, the imaging system 100 may be connected to a network (e.g., a telecommunications network, a local area network (LAN), a wireless network, a wide area network (WAN) such as the Internet, a peer-to-peer network, a cable network, etc.) for communication purposes.

The description above is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the reconstruction unit 225 may be included in a graphics processing unit (GPU).

Figure 3:
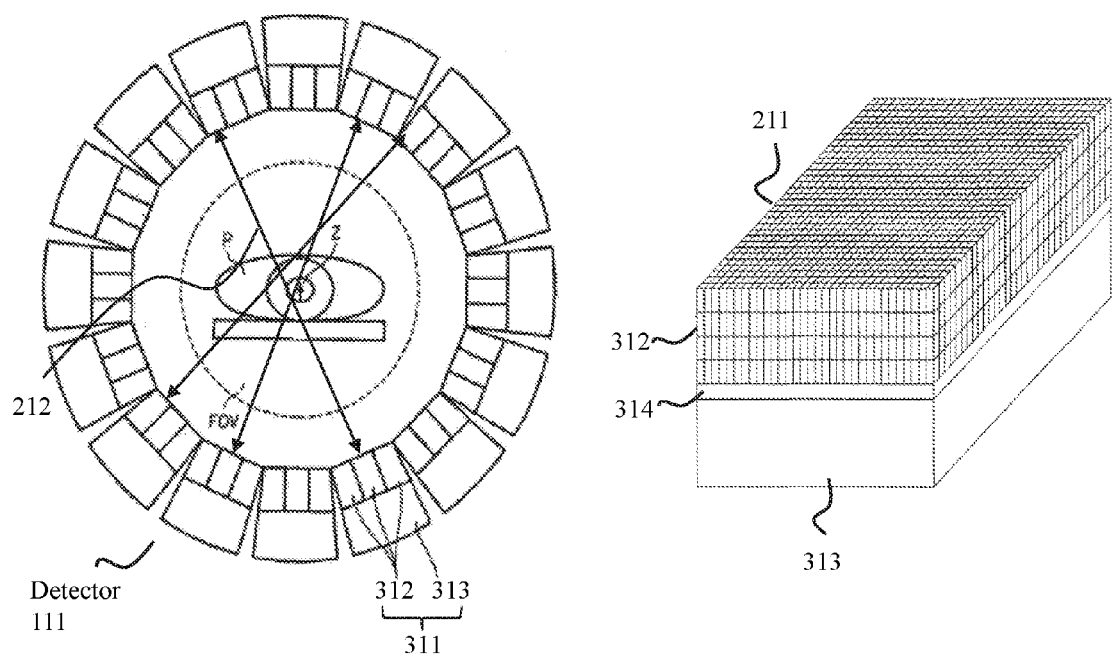
FIG. 3 is a perspective view of a detector according to some embodiments of the present disclosure.

FIG. 3 is a perspective view of the detector 111 according to some embodiments of the present disclosure. As shown in FIG. 3, a detector cell 311 in the detector 111 may include a scintillator 312, a light guide 314, and a photodetector 313. In some embodiments, the photodetector 313 may be photomultiplier (PMT). The light guide 314 may be optically coupled to the scintillator 312 to provide a light path to the photodetector 313. It should be noted that the detector cell described below is merely provided for illustration purposes, and not intended to limit the scope of the present disclosure. In some embodiments, the scintillator 312 may include an array of scintillation crystals, the detector cell 311 may include more than one photodetector. Incident gamma rays may strike the scintillator 312 to produce small bursts of visible or invisible light. The visible or invisible light may be converted to an electric signal (e.g., an electric pulse) by, for example, a photocathode of the PMT. In some embodiments, the electric pulse may be generated by amplifying electrons excited by the visible or invisible light through a dynode string in the PMT.

In should be noted that the photodetector may be but not limited to PMT. In some embodiments, the photodetector may be a silicon photomultiplier (SiPM), an avalanche photodiode (APD), or the like, or a combination thereof. Actually, any kind of sensor functioning as photovoltaic conversion may be suitable in the present disclosure.

The scintillator may include different kinds of compounds. Exemplary compounds may include Bismuth germinate (BGO), barium fluoride (BaFl), gadolinium silicate (GSO), Lutetium orthosilicate (LSO), Lutetium Yttrium orthosilicate (LYSO), or the like, or a combination thereof.

Figure 4:
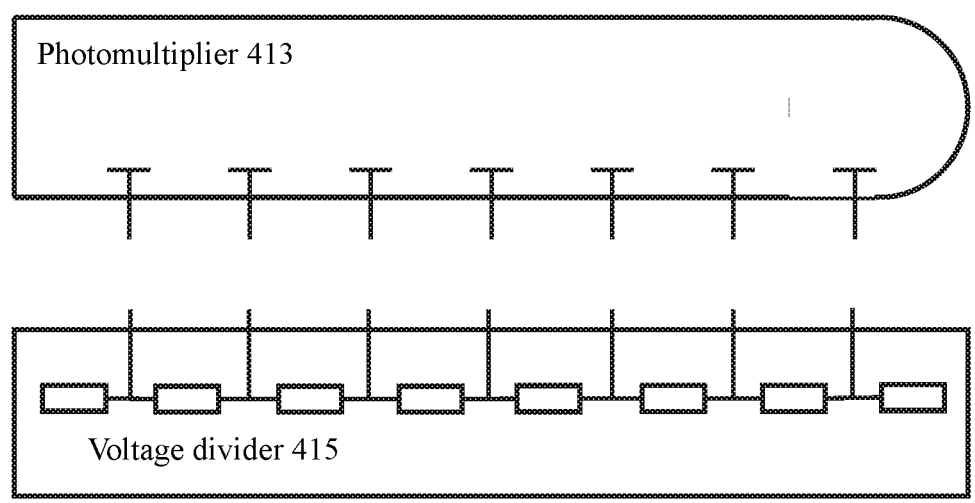
FIG. 4 is a diagram of a photomultiplier and a voltage divider according to some embodiments of the present disclosure.

In some embodiments, a PMT may include a photocathode, multiple dynodes, and an anode. Incident photons may strike the photocathode to generate electrons. A photocathode may include a thin conducting layer on the inside of the entry window of the PMT. These electrons may be directed by a focusing electrode toward an electron multiplier, wherein electrons generated in response to the incident photons may be multiplied by the process of secondary emission. The electrons generated in response to the incident photons may strike an electrode in a vacuum tube to cause the emission of additional electrons. To guide the movement of electrons, the distribution of voltage along the series of dynodes may be determined by a voltage divider 415 as shown in FIG. 4. As shown, the photomultiplier 413 and the voltage divider 415 may be coupled together, by a welding method. In some embodiments, the voltage divider may include a plurality of elements. Exemplary elements may include a resistor, a capacitor, or the like, or a combination thereof.

Figure 5:
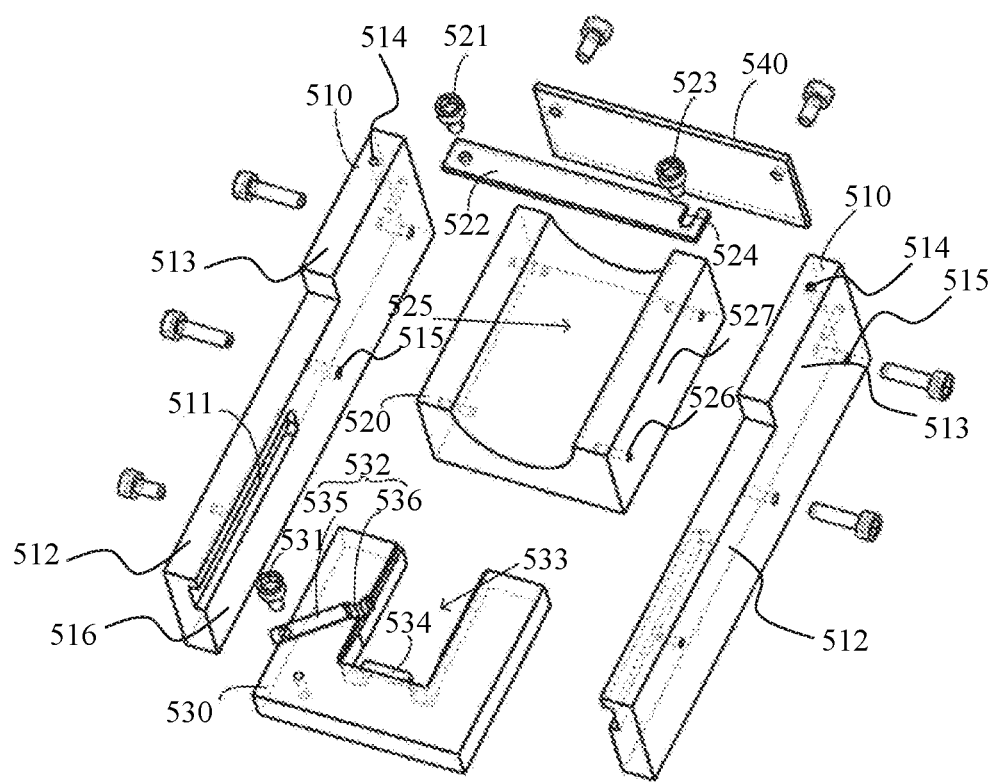
FIG. 5 illustrates an exemplary welding device according to some embodiments of the present disclosure.

An exemplary welding device for welding a photomultiplier and a voltage divider is illustrated in FIG. 5. The welding device 500 may include a pair of side plates 510, a PMT holding part 520, a voltage divider platform 530, and a back baffle 540.

The voltage divider platform 530 may include a groove 533, a stage 534 within the groove 533 for holding a voltage divider (not shown in FIG. 5), a reed 532, and a fasten bolt 531. The reed 532 may include a stiff end 535 and an elastic end 536 such that the stiff end 535 may rotate around the fasten bolt 531 to hold a voltage divider in place on the stage 534. Thus, the voltage divider may be placed on the voltage divider platform 530.

The PMT holding part 520 may include a PMT holding tank 525, a reed 522, a bayonet 524 on the reed 522, a first fasten bolt 521, and a second fasten bolt 523. As shown in FIG. 5, the side plates 510 may include a front part 512 and a back part 513 forming a stage on the top surfaces. The top surfaces of the front part 512 and the back part 513 may be parallel to each other. There may be bores 514 on the top surfaces of the side plates 510, through which the first fasten bolt 521 and the second fasten bolt 523 may be screwed onto the corresponding side plates 510. The bayonet 524 may allow the reed 522 to rotate around the first fasten bolt 521 for fixing and removing a PMT. After holding the PMT in the PMT holding tank 525, the reed 522 may rotate, e.g., counterclockwise, around the first fasten bolt 521 to the bayonet 524 until the second fasten bolt 523 fixes the PMT into the PMT holding tank 525. The reed 522 may rotate, e.g., clockwise, around the first fasten bolt 521 to release the PMT.

There may be several through-holes 515 in the side plates 510 and corresponding bores 526 in two outer side surfaces 527 of the PMT holding part 520. Multiple fasten bolts may be used for fixing the side plates 510 onto the PMT holding part 520. At least two guiding slots 511 may be set on the inner side surfaces 516 of the side plates 510. In some embodiments, the guiding slots 511 may guide the forward and backward movement of the voltage divider platform 530 or the PMT holding part 520, so that at least one point (e.g., a pin) on the PMT may align with a corresponding point on the voltage divider. To achieve the guiding process, the length of the side plates 511 may be set longer than the length of the PMT holding part 520. The back baffle 540 may be fixed with the two side plates 510 or the PMT holding part 520 by, for example, two screws, to constrain the movement of the PMT. Thus, the PMT may be positioned and its one or more pins may be aligned by the unilateral movement of the voltage divider platform 530 guided by the guiding slot 511.

Figure 6:
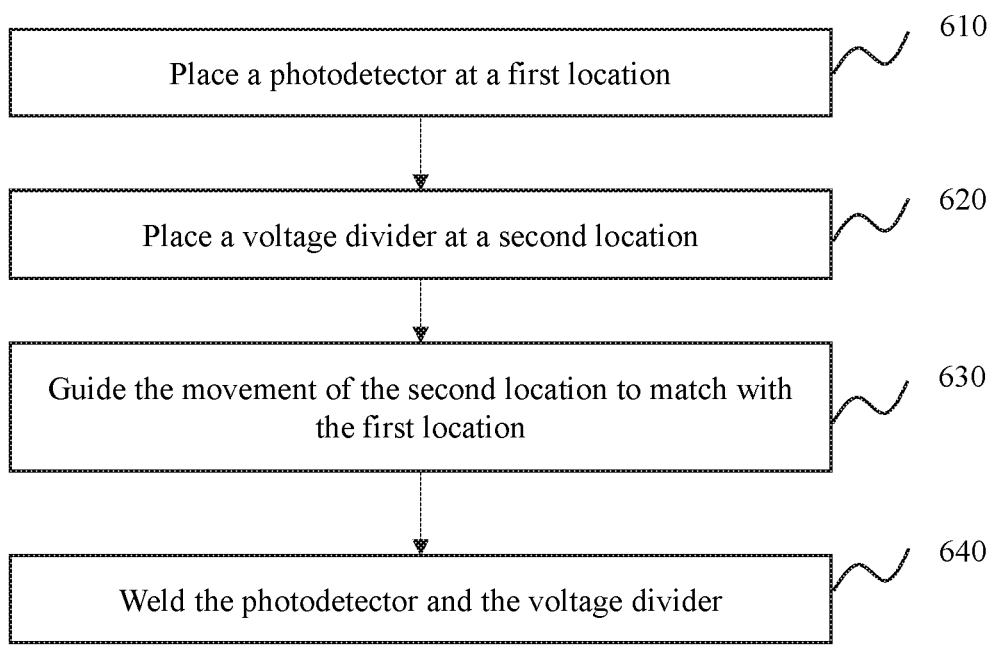
FIG. 6 shows a flowchart of a welding process according to some embodiments of the present disclosure.

FIG. 6 shows a flowchart of the welding process according to some embodiments of the present disclosure. The photodetector may be placed at a first location in step 610. For example, a PMT may be placed in the PMT holding tank 525. According to the embodiments as described above, the back end of the PMT may be refrained by the back baffle 540, the reed 522 may rotate, for example, counterclockwise, around the first fasten bolt 521 to match with the bayonet 524, and the second fasten bolt 523 may screw up tightly to fix the PMT in the PMT holding tank 525. In step 620, a voltage divider may be placed at a second location. For example, the voltage divider may be placed on the stage 534 in the groove 533 of the voltage divider platform 530. The reed 532 may rotate around the fasten bolt 531 to move the elastic end 536 to hold the voltage divider in place on the stage 534. Next, the second location and the first location may be moved to align with each other in step 630. For example, the voltage divider may be guided forward and/or backward to/from the PMT by way of moving the voltage divider platform 530. In step 640, the photodetector and the voltage divider may be welded together.

Besides the physical property as described above, there may be other aspects that may affect the working condition of PMT. For example, in a PET system, the output of the PMT may shift with temperature. The disclosure herein may provide a testing or calibrating method on the working condition of the PMT.

Figure 7A:
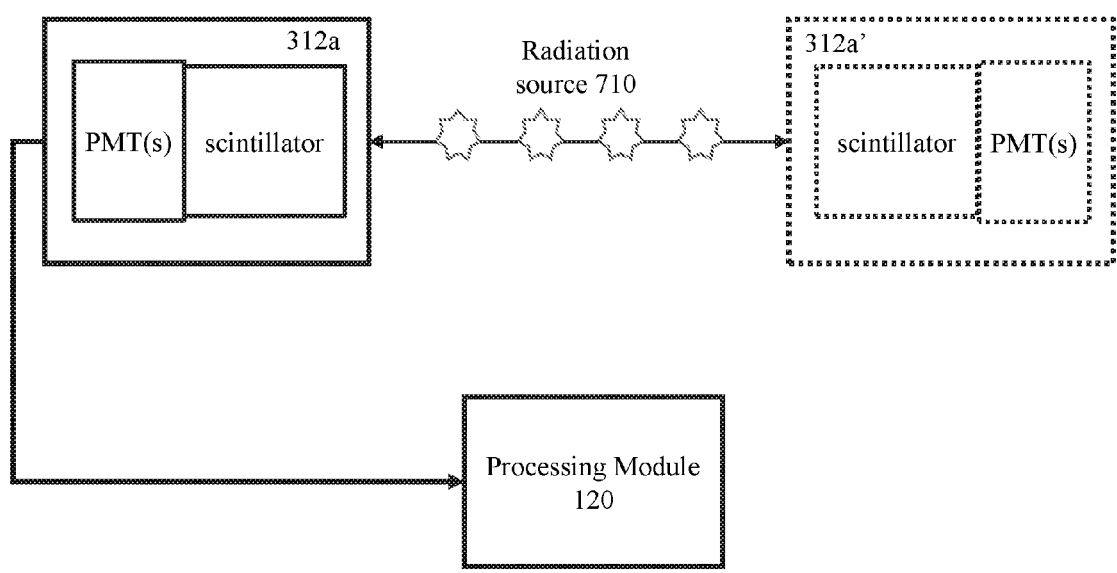
FIG. 7A-FIG. 7C illustrate different ways of generating radiation that may be incident on a PMT according to some embodiments of the present disclosure.
Figure 7B:
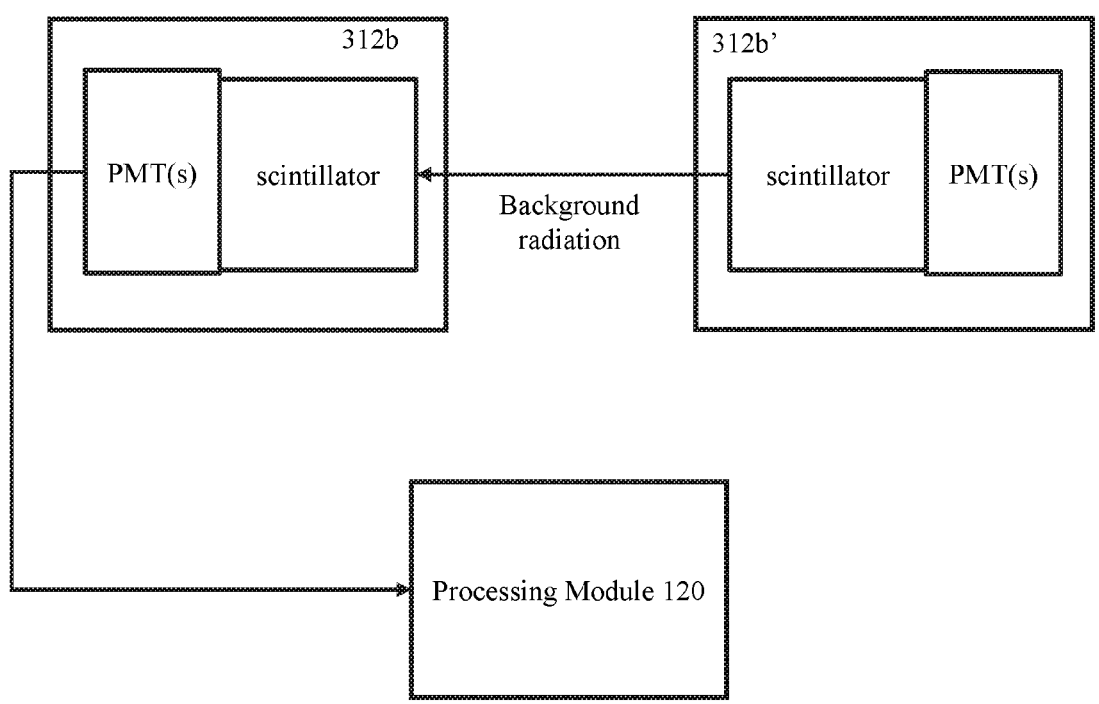
Figure 7C:
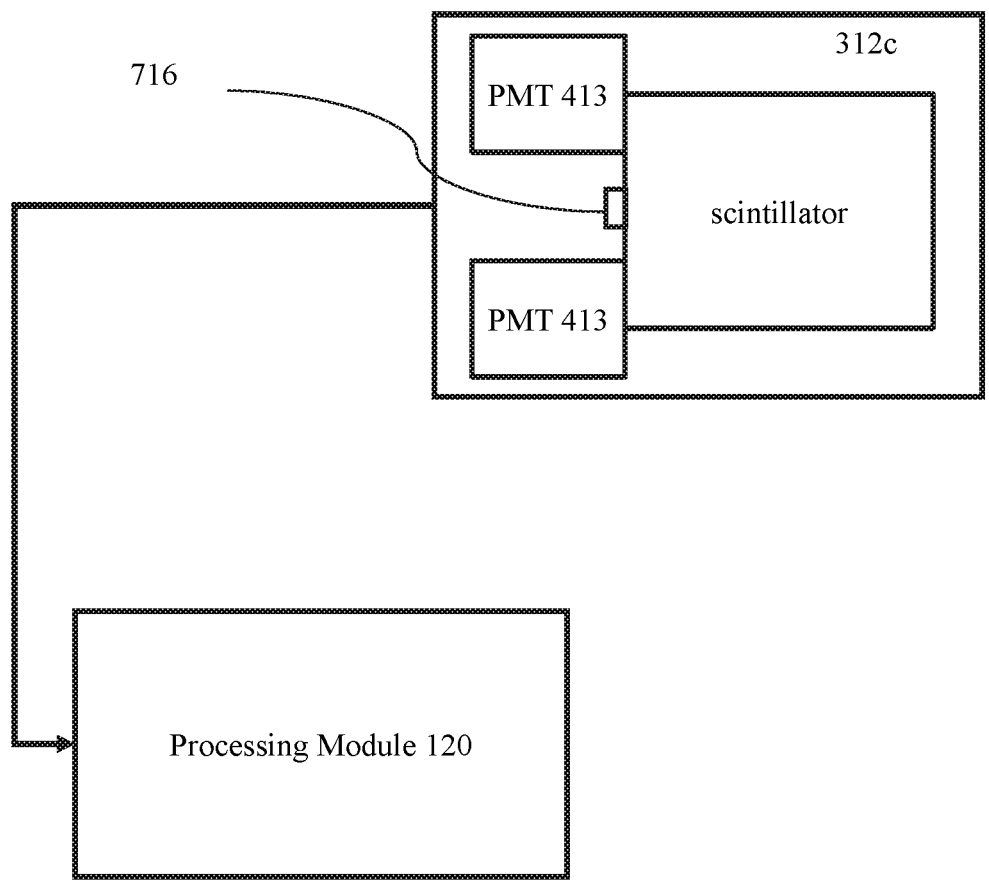

In order to test or calibrate the PMT, a specific radiation may be used. FIG. 7A, FIG. 7B, and FIG. 7C illustrate different ways of generating radiation that may be incident on a PMT according to some embodiments of the present disclosure. As shown in FIG. 7A, a radiation source 710 may be used to generate electrons. The radiation source 710 may radiate gamma rays that may be detected by the scintillators. In some embodiments, the radiation from the radiation source 710 may be uniformly distributed. Light produced by the scintillator 312a and 312a' may transmit to a photodetector, such as a PMT, to convert the light into electrical pulses. In some embodiments, the electrical pulses may be processed in the processing module 120 in a manner that the time information of at least some of the electrical pulses may be recorded for further analysis when a certain condition is satisfied. For instance, the condition may be that the amplitude of an electric pulse is above or lower than a reference voltage.

In some embodiments, the radiation source may be unnecessary. As shown in FIG. 7B, a scintillator 312b may receive characteristic radiation (also referred to as "background radiation") from a scintillator 312b' corresponding to another detector cell. The characteristic radiation may excite the scintillator 312b to produce light, and the produced light may be further transmitted to the photodetector. It should be noted that FIG. 7B is for illustration purposes, not intended to limit the scope of the disclosure. In some embodiments, a detector cell may receive its own characteristic radiation to produce light. The scintillators may emit a certain amount of radiation. For example, Lutetium orthosilicate (LSO) and Lutetium Yttrium orthosilicate (LYSO), which may be used as crystals in scintillators, may include radioactive isotopes of lutetium (Lu176). The Lu176 may release a beta ray and three gamma rays when it decays, at 88 keV, 202 keV, and 307 keV.

FIG. 7C shows another radiation that may be used to test or calibrate a PMT of a detector cell according to some embodiments of the present disclosure. As shown, a light source 716 may be set on a back end of a scintillator 312c with two PMTs 413 located symmetrically on the same side of the scintillator 312c. As used herein, the light source 716 may be used as an external source and produce visible light that may be detected by the PMT. In some embodiments, the light source 716 may be a LED or a part of a fiber that may output light into the scintillator. A half portion of a PMT may attach to the scintillator 312c, and the other half portion may attach to another scintillator (not shown in FIG. 7C). With this design, each scintillator may correspond to a PMT and the light source may be guided by the scintillator and reflected into the PMTs. There may be a reflective layer on at least one of the surfaces of the scintillator so that the light from the light source 716 may be reflected and directed into the PMTs. In some embodiments, the scintillator may be a hexahedron, a parallelepiped, etc. Multiple surfaces of the scintillator may be coated with the reflective layer. Merely by way of example, a hexahedron scintillator may be coated with a reflective layer on every surface except the surface that the PMTs may contact. Then, the PMTs may output signals relating to electric pulses to the processing module 120 for subsequent processing. The description above is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the location of the light source 716 may be different from that as illustrated in FIG. 7C. In some embodiments, the light source 716 may be placed on the other side of the scintillator (e.g., the front end). As another example, different scintillators corresponding to different detector cells may share a common light source, or use different light sources respectively.

The stability of the performance of a scanner during an imaging (or scanning) process may impact image reconstruction. As used herein, the stability may denote that when a same set of operation parameters or settings are used, the obtained images corresponding to a same scanned object may be similar or without an obvious deviation. To stabilize the performance of a scanner, one of the factors may relate to the performance of the one or more photodetectors. The performance of a photodetector may be tested based on the testing as described in connection with FIGS. 7A-7C. Merely by way of example, as described elsewhere in the disclosure, the output signal of a PMT may shift with time. In some embodiments, the calibration of the PMT may be realized by adjusting the electron gain of the PMT. An individual PMT may be calibrated according to a calibration process. The calibration of the PMT may be executed once in a certain period of time. In some embodiments, the PMT may be calibrated every other week. In some embodiments, the calibration may be executed when the quality of the image obtained is unsatisfactory due to, for example, the output shift of the PMT. In some embodiments, a determination may be made as to whether a PMT in a detector cell works properly from time to time (e.g., periodically). For instance, such a determination may be performed every day before the PET scanner is used for the first time during the day.

Figure 8:
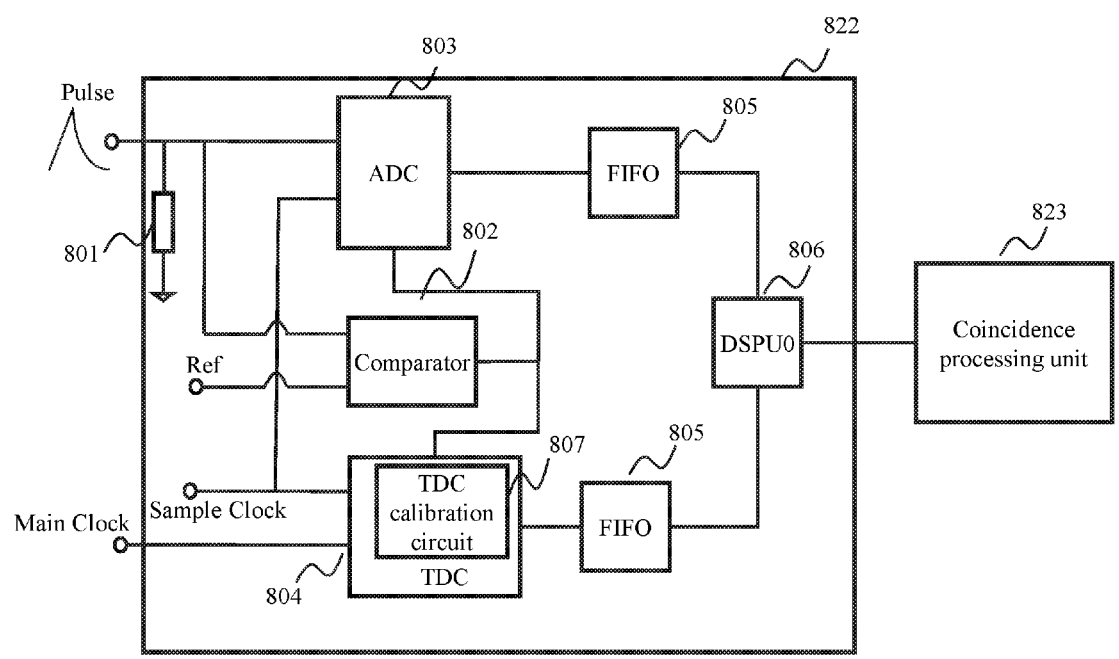
FIG. 8 is a block diagram of a data acquisition unit according to some embodiments of the present disclosure.

FIG. 8 is a block diagram of the data acquisition unit 221 according to some embodiments of the present disclosure. As shown in the figure, the data acquisition unit 221 may include a signal acquisition and processing block 822 and a coincidence block 823. The signal acquisition and processing block 822 may be used to sample the electrical pulses at an appropriate sampling rate and digitally process the sampled pulses to derive relevant information for PET imaging. In some embodiments, the relevant information may include a single event count, the energy of a single event, the time of a single event, parameters describing the pulse shape acquired by the data acquisition unit 221, or the like, or a combination thereof. The relevant information obtained in the signal acquisition and processing unit 822 may be transferred to the coincidence processing unit 823 to determine the position of, for example, an annihilation in a PET system. As used herein, a single event may correspond to a photon incident on a photodetector or a radiation ray incident on a scintillator. Because an electrical pulse may correspond to one or more single events, the event energy or the single event count may denote the energy or time of one or more specific single events represented by the form of electrical pulses. In some embodiments, multiple signal acquisition and processing units 822 may be connected to a coincidence processing unit 823. The processing unit 822 and the coincidence processing unit 823 may be connected through a number of channels. In some embodiments, depending on the number of channels, multiple coincidence processing units 823 may be employed when needed. For example, when the number of channels is such that a coincidence processing unit 823 is overburdened, more coincidence processing unit 823 may be employed.

In the signal acquisition and processing unit 822, the input signal may be an electrical pulse generated by the photodetector, and a main clock signal indicating the system time. In some embodiments, the electrical pulses may be converted to voltage pulses by a resistor 801. The resistance of the resistor 801 may be 50Ω, or 40Ω, or any positive number.

The signal acquisition and processing unit 822 may include an analog-to-digital convertor (ADC) 803, a time-to-digital convertor (TDC) 804, at least one first-in-first-out (FIFO) 805, and a digital signal processing unit (DSPU) 806. After converted by the resistor 801, the voltage pulse signal may be divided into two portions. The first portion may be transmitted to the ADC 803 as an energy signal relating to a radiation event, and the other portion may be transmitted to a time-to-digital convertor (TDC) 804 through a comparator 802 as a time signal relating to the radiation event. In some embodiments, the comparator 802 may be configured to determine whether an input signal is a noise signal. A sample clock may be connected to the ADC 803 and also to the TDC 804 to synchronize the sampling rate of the ADC 803 and of the TDC 804. The first portion of the voltage pulse signal may be sampled by the ADC 803 to generate a first digital signal. The first digital signal may be stored in a first FIFO 805. The second portion of the voltage pulse signal transmitted to the TDC 804 may be processed and output as a second digital signal containing the time of the sampling with respect to the system time (i.e., the main clock). The second digital signal may be stored in a second FIFO 805. The DSPU 806 may be configured to analyze the first digital signal generated by the ADC 803 and the second digital signal generated by the TDC 804. In some embodiments, one or more single event parameters relating to PET imaging may be obtained by the DSPU 806. Exemplary single event parameters may include the number of single events (or referred to as single event count), energy relating to a single event, time distribution of single events, pulse-shape related parameters (e.g., amplitude, width, etc.), or the like, or a combination thereof. One or more signal-processing algorithms may be implemented to provide an estimation of the single event parameters in accordance with the characteristics of the electrical pulses and the noise. In some embodiments, algorithms may also be implemented in the DSPU to detect pile-up events and apply corrections to reduce pile-up errors. In the DSPU 806, the event time may be estimated according to the ADC samples and TDC samples, based on which the coincidence processing unit 823 may determine the corresponding parameters of a coincidence event.

In the data acquisition unit 221, the linear performance of the TDC 804 may affect the quality of the event parameter estimation in the DSPU. A mismatch among an assembly of time delay cells in the TDC may lead to a nonlinear performance of the TDC. In some embodiments, a TDC calibration circuit 807 may be used to calibrate the output of the TDC. The output signal may be processed in the TDC calibration circuit 807 such that the output digital signal may contain the actual time information relating to the corresponding event. In some other embodiments, the calibration method may be realized by a software implemented in the DSPU 806 or other processing unit in the system.

It should be noted that the above description of the data acquisition unit 221 is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure. For example, the calibration for the digital signal output from the TDC 804 may not be necessary. If the requirement of the resolution of the PET image is not high for a certain kind of disease diagnosis, and the image error caused by the deviation of the output signal by the TDC 804 may be ignored, the calibration for the TDC calibration may be unnecessary. As another example, the output from the ADC 803 and the TDC 804 may be directly transmitted to the DSPU 806 without being stored in the FIFO 805.

Figure 9:
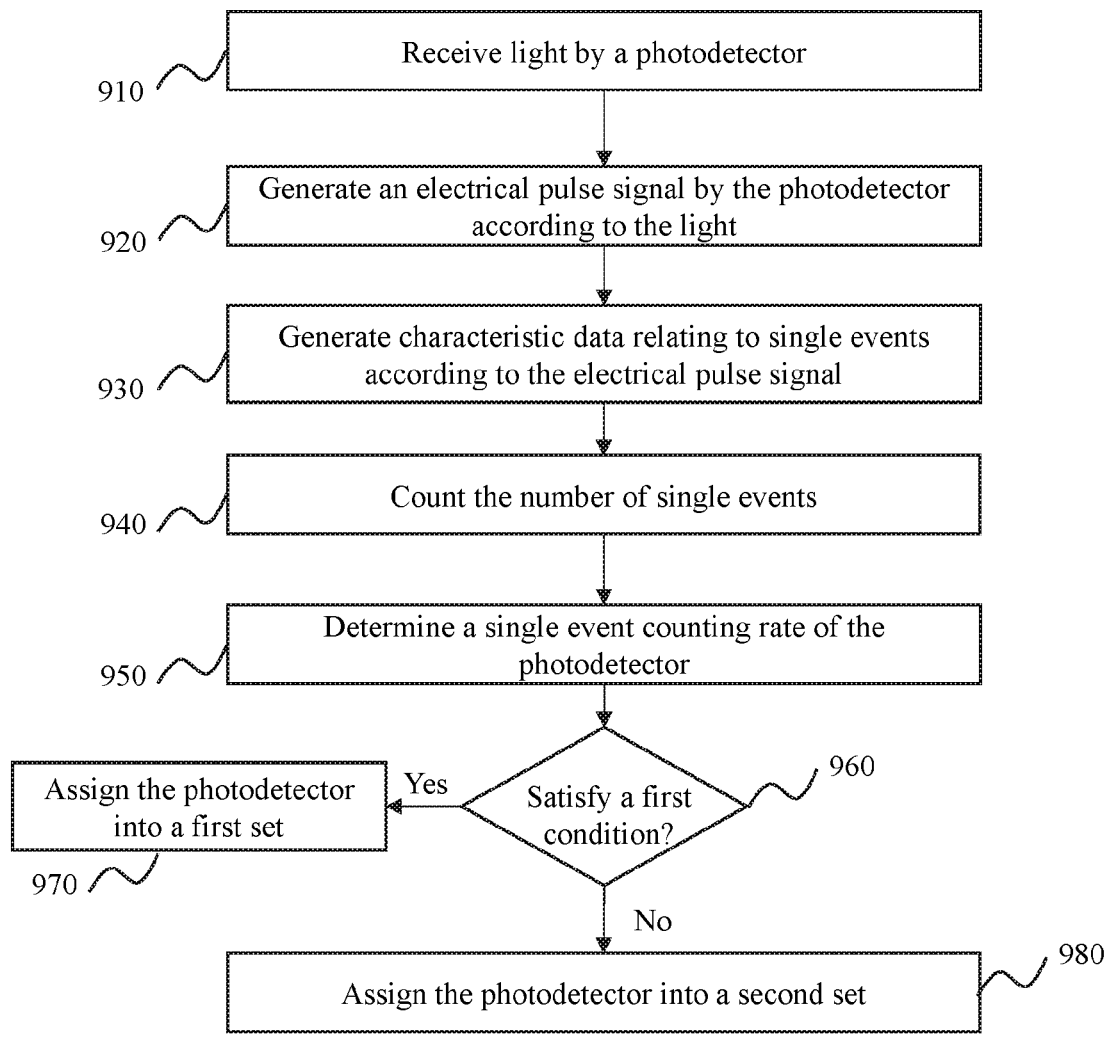
FIG. 9 is a flowchart illustrating a method of testing a photodetector according to some embodiments of the present disclosure.

FIG. 9 is a flowchart illustrating a method for testing a photodetector according to some embodiments of the present disclosure. In step 910, the photodetector may receive light. In some embodiments, the light may be generated by a scintillator in response to a characteristic radiation from another scintillator, or radiation from a radiation source. In some embodiments, the light may be generated directly by an external light source. The light emitted from the external light source may satisfy some conditions. For example, the wavelength of the light may be detectable by the photodetector, or the intensity of the light may be suitable for the photodetector. Details regarding how the light is generated may be found elsewhere in the present disclosure at, for example, FIGS. 7A-7C.

In step 920, an electrical pulse signal may be generated by the photodetector in response to the light received. As described elsewhere in the disclosure, an electrical pulse may correspond to one or more single events detected by the photodetector. In some embodiments, the intensity of light may determine the number of incident photons that may further determine the number of the electrical pulses. For example, a higher intensity of light may correspond to more electrical pulses. As is shown in FIG. 8, the electrical pulse signal may be detected by a signal acquisition and processing unit 822 and prepared for further processing.

In step 930, characteristic data relating to single events may be generated according to the electrical pulse signal. The characteristic data relating to single events may include the time distribution of the single events, the energy relating to a single event, or the like, or a combination thereof. For example, the electrical pulse signal may be analyzed by the ADC 803 and output a digital signal including the number of the single events. The time information of the single events may be extracted by the TDC 804 and output as another digital signal. Both of the digital signals may be processed in the DSPU 806 and further transmitted to the coincidence processing unit 823. A coincident event may be determined according to the digital signal output from the DSPU 806. In some embodiments, the characteristic data of single events may be stored in a memory for further use.

In step 940, the number of the single events may be counted. Specifically, the number of single events detected by a specific photodetector may be counted based on the electrical pulse signal. In some embodiments, the detected single events on the specific photodetector may be evaluated to determine whether the photodetector is in a suitable working condition. In some embodiments, step 940 may be finished within a certain time period. Merely by way of example, the time period may be a predetermined PET scanning time interval. The time interval may be 1 minute, 6 minutes, 60 minutes, or the like. In some embodiments, step 940 may be terminated based on other criterions. For instance, step 940 may be terminated when the amount of data stored in the data storage unit exceeds a threshold, such as, 10 G, 20 G, or the like.

In step 950, a single event counting rate of the photodetector may be determined. As used herein, the single event counting rate may be identified as a ratio of the number of single events detected by one photodetector to the total number of single events detected by some or all photodetectors of the detector of a PET scanner.

In step 960, the working condition of the photodetector may be evaluated based on the counting rate of the photodetector. If the single event counting rate of the photodetector satisfies a first condition, the process may proceed to step 970 and the photodetector may be assigned into a first set. Otherwise, the process may proceed to step 980 and the photodetector may be assigned into a second set. In some embodiments, the first condition may be that the single event counting rate of the photodetector is within a range. The range may be determined based on a threshold. In some embodiments, the first condition may be that the single event counting rate of the photodetector is equal to or exceeds a certain threshold. For instance, the threshold may be a number of a range (or referred to as threshold range) that is predetermined by an operator of the PET scanner or according to a setting of the PET scanner (e.g., provided by the manufacturer of the PET scanner). As another example, the threshold may be determined empirically. As a further example, the threshold may be determined according to at least some of the operating parameters of the PET scanner. Specifically, the radiation emitted from the radiation source placed in the FOV of the PET scanner may be stronger than the background radiation emitted from the scintillator. Thus, the threshold when a radiation source in the FOV of the PET scanner is used for testing may be different from the threshold when background radiation emitted from the scintillator is used for testing because of the differences in the intensities of radiation from the scintillator and from the radiation source in the FOV. In some embodiments, the threshold may be stored in a data storage unit 223 as is shown in FIG. 2. In some embodiments, the threshold range may be dynamically changed according to the single event counting rate. For example, the threshold may be set as an average value of the single event counting rates in respect to some or all of the photodetectors in a PET scanner. In some embodiments, the first set may be considered as a set of suitable photodetectors. In some embodiments, a photodetector assigned in the first set may be further tested by another testing method to confirm fits suitability. The photodetector assigned in the second set may be considered as unsuitable, and it may also be further tested to confirm its unsuitability. Exemplary methods of further processing may be found at, for example, FIG. 10 and the description thereof.

It should be noted that the above description of the method of determining whether a photodetector is eligible is provided for the purposes of illustration, not intended to limit the scope of the present disclosure. For example, in some embodiments, step 950 may be replaced by comparing the number of single events with a threshold. In some embodiments, the single event counting rate may be calculated directly by a circuit or a processor without step 940. In some embodiments, the threshold may be set as a constant value or a range, or may be set as different values or ranges for different photodetectors according to the characteristics thereof. For persons having ordinary skills in the art, various variations and modifications may be conducted under the teaching of the present disclosure. However, those variations and modifications may not depart the protecting scope of the present disclosure.

Figure 10:
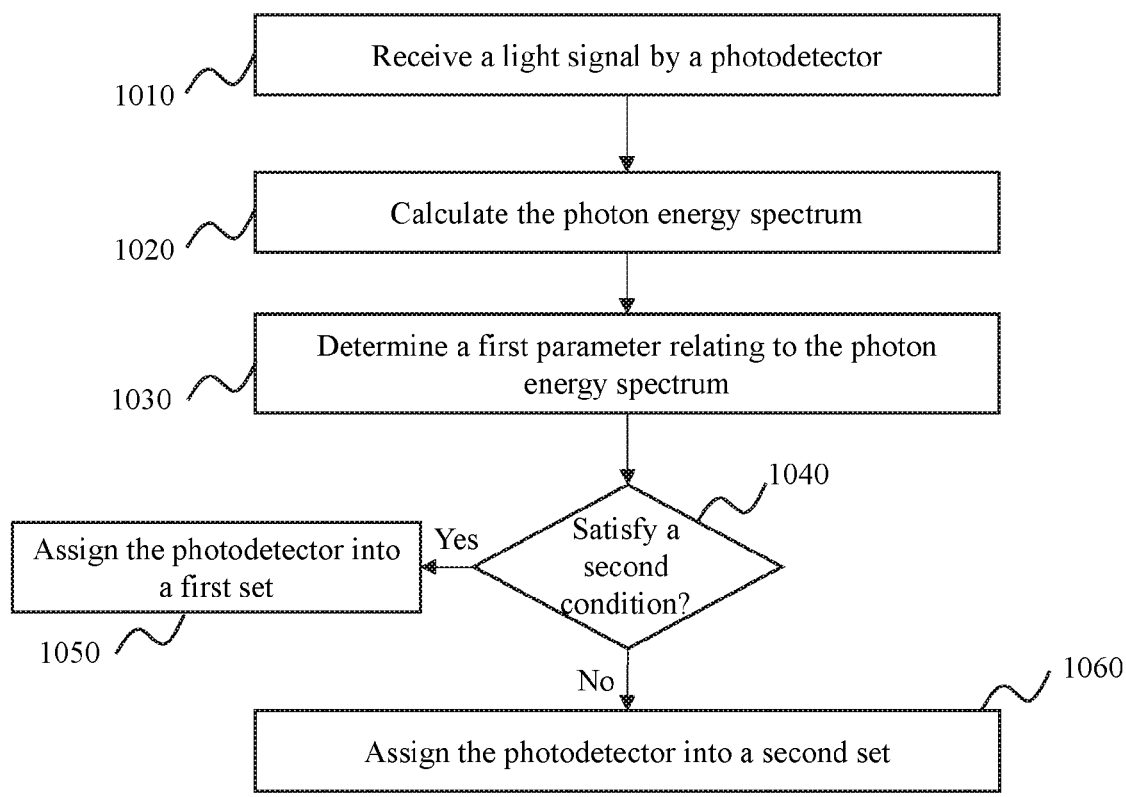
FIG. 10 is a flowchart illustrating a method of testing a photodetector according to some embodiments of the present disclosure.

FIG. 10 is a flowchart illustrating a method for testing a photodetector according to some embodiments of the present disclosure. In step 1010, light may impinge on a photodetector. The description of this step may be similar to that in step 910. In step 1020, a photon energy spectrum of the light may be calculated. The spectrum may be calculated according to an electrical pulse signal generated by the photodetector. In some embodiments, the light generated by the scintillator 312 in response to a radiation ray may contain energy information of the radiation ray. For example, the background radiation generated from $^{176}$Lu may generate three types of gamma rays with characteristic energy peaks of 307 keV, 202 keV, and 88 keV when decaying. As another example, radiation from a radiation source may also contain one or more characteristic energy peaks. As a result, the electrical pulse signal generated by a photodetector may contain information regarding the characteristic energy peak of the radiation ray. The electrical pulse signal may be further processed in the processing module 120 to calculate the photon energy spectrum. As used herein, the characteristic energy peak (or referred as characteristic peak) may denote the inherent energy distribution of the radiation of a radiation source.

In step 1030, a first parameter relating to the spectrum may be determined. In some embodiments, the first parameter may relating to at least one peak in the photon energy spectrum. For example, the position of the at least one peak may be determined. As another example, the relative position of two or more peaks may be determined. In some embodiments, the first parameter may be identified as the deviation between the position of the at least one peak in the calculated spectrum and the position of the corresponding characteristic peak(s) of the radiation source or the background radiation. In some embodiments, the first parameter may be identified as the deviation between the intensity of the at least one peak in the calculated spectrum and the intensity of the corresponding characteristic peak(s) determined by the radiation source or the background radiation. In some embodiments, the first parameter may be identified as the deviation between the positions of two or more peaks in the calculated spectrum and the positions of the corresponding characteristic peaks of the radiation source or the background radiation.

In step 1040, the working condition of the photodetector may be evaluated. In some embodiments, if the first parameter satisfies a second condition, the process may proceed to step 1050 and the photodetector may be assigned into the first set as described in FIG. 9. Otherwise, the photodetector may be assigned into the second set as described in FIG. 9. The second condition may be that the first parameter does not exceed a threshold. For example, in the case when the first parameter is identified as the deviation between the position of one peak in the calculated spectrum and the position of the corresponding characteristic peak, if the deviation is below a threshold, the second condition is satisfied. Otherwise, the second condition is not satisfied. In some embodiments, the photodetector assigned into the first set may be further tested to confirm its suitability.

In some embodiments, the method described in FIG. 9 may be used together with the method described in FIG. 10. For example, if the two methods are applied together, the photodetector that satisfies both the first condition and the second condition may be considered suitable. On the other hand, the photodetector that satisfies neither the first condition nor the second condition may be consider as unsuitable and may need to be calibrated; otherwise, the photodetector may be considered suitable and need not to be calibrated.

Figure 11:
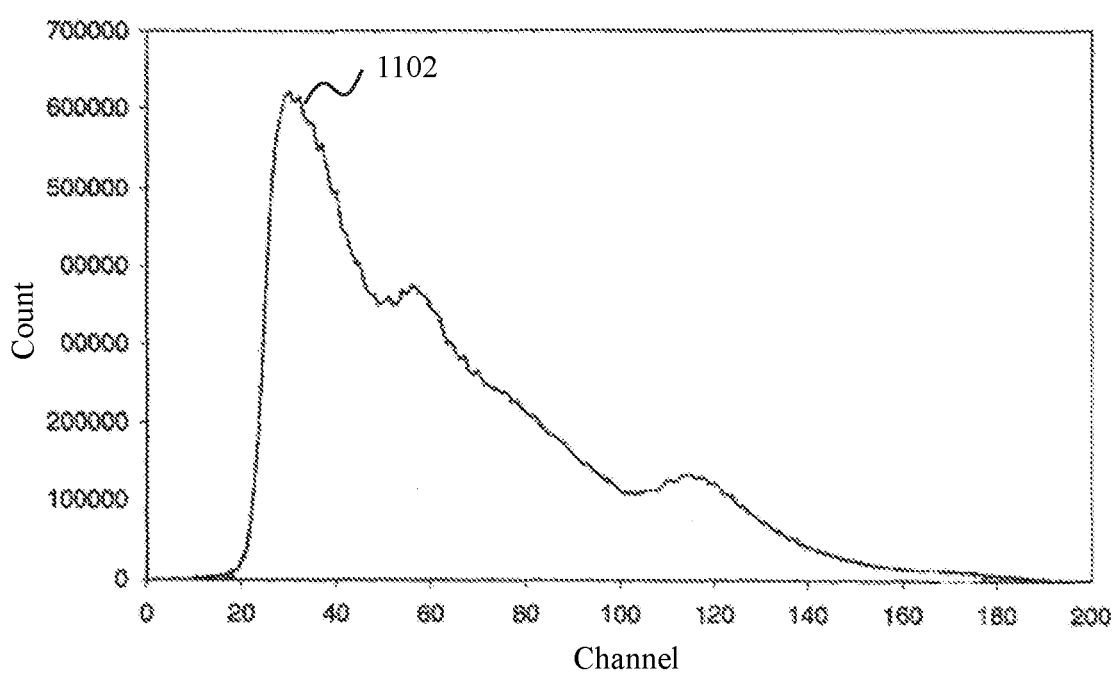
FIG. 11 and FIG. 12 are two examples of a photon spectrum according to some embodiments of the present disclosure.
Figure 12:
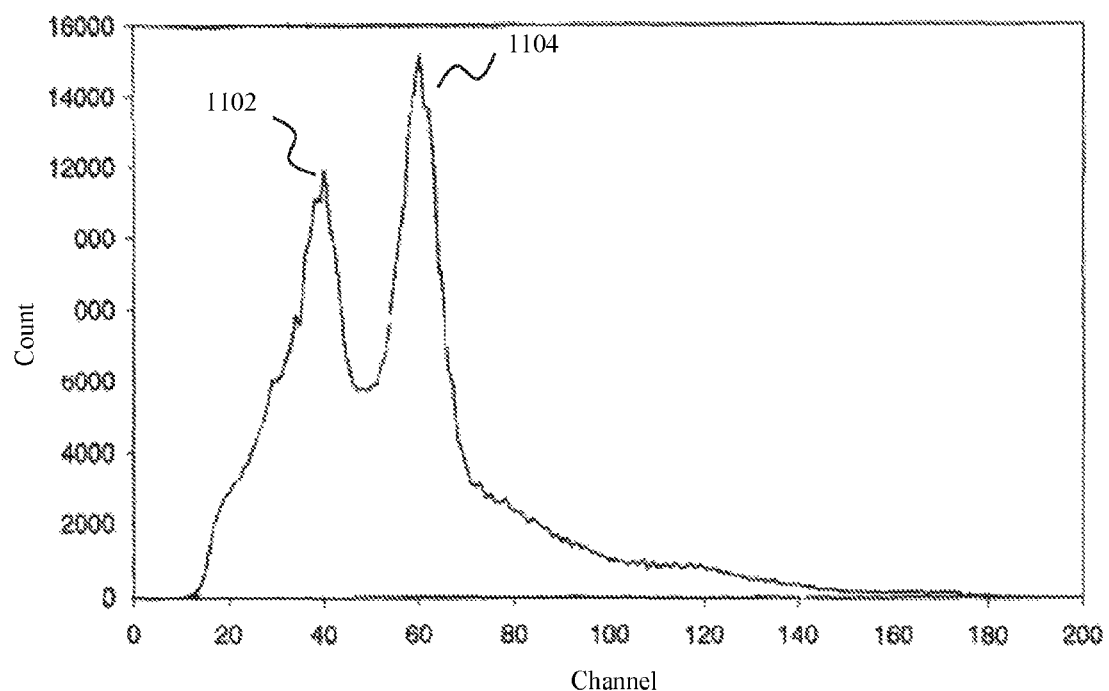

FIG. 11 and FIG. 12 are two examples illustrating the peaks in the calculated photon spectrum according to some embodiments of the present disclosure. In both examples, the radiation source is the background radiation generated by Lu176. In FIG. 11, the spectrum may be calculated under a single photon mode that only the energy peak corresponding to 202 keV may be calculated. The position of the peak 1102 may be compared with the position of the characteristic peak of 202 keV. If the deviation exceeds a threshold, the corresponding photodetector may be considered unsuitable. In FIG. 12, the spectrum may be calculated under a complex mode that both the energy peaks corresponding to 202 keV and 307 keV may be calculated. The peak 1104 may be considered as the peak corresponding to 307 keV. If the relative position between the peak 1102 and the peak 1104 deviates from the relative position of the corresponding characteristic peaks, and the deviation exceeds a threshold, the corresponding photodetector may be considered unsuitable.

In some embodiments, the testing result of the photodetector may be output to a user in the form of, for example, an onscreen display. In some embodiments, the testing method may be executed manually when needed. In some embodiments, the testing method may be executed automatically. For example, the testing method may be executed before the PET scanner is used for the first time during a day.

In some embodiments, after the suitability of photodetectors are determined, a calibration process may be performed to calibrate the ineligible photodetectors. The calibration method may not be limited to what is illustrated in the present disclosure. The calibration method may be performed manually or automatically by a software program. For example, if a calibration program is pre-stored in the PET scanner, the calibration method may be executed automatically after the ineligible photodetectors are identified.

Figure 13:
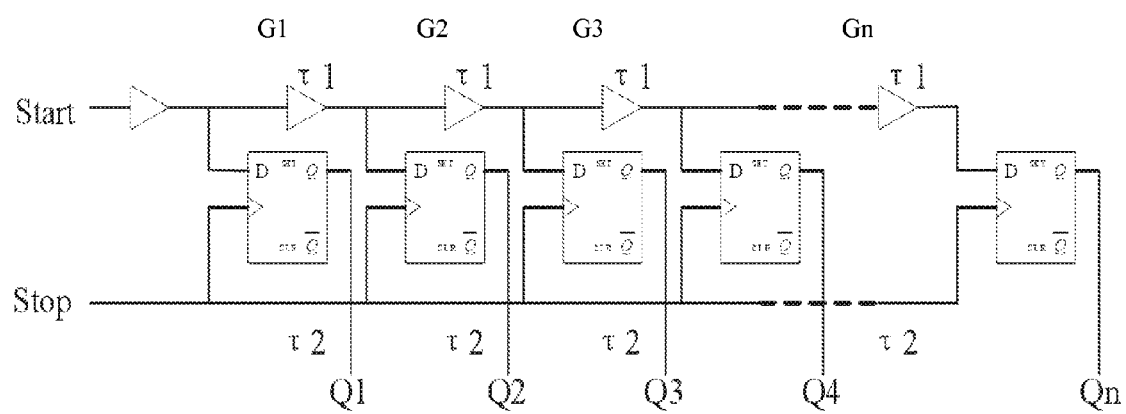
FIG. 13 is a schematic circuit diagram of an exemplary Time-to-Digital (TDC) according to some embodiments of the present disclosure.

Referring back to the signal acquisition and processing unit 822 illustrated in FIG. 8, the TDC 804 may be configured to extract the time information of the electrical pulse signal. In FIG. 13, a schematic circuit diagram of an exemplary time-to-digital converter (TDC) is shown according to some embodiments of the present disclosure. The TDC may be based on a tapped delay-line structure, in which the start signal may be fed. The start signal may be the signal carrying the time information to be converted. The delay-line may contain a number n of delay elements, or cells, or the like, or a combination thereof. The delay elements may introduce an elementary delay time. For instance, the delay elements may be logic gates $G_1$ to $G_n$ cascaded in series. The logic gates may be any type suitable for the application. Exemplary types may include a pass-gate, an inverter, a buffer, a NAND (negative-AND) gate, a NOR-gate, or the like, or a combination thereof. When propagating through the delay-line, the start signal may be delayed. The TDC may further include a number n of sampling elements $S_1$ to $S_n$ (not shown in FIG. 13). The sampling elements may be respectively connected to the outputs of the delay elements. The sampling elements may be adapted to sample the state of the delay-line on the rising edge of the stop signal. For example, a sampling process may be performed to freeze the state HIGH or LOW of the delay elements of the delay-line at the point in time when the stop signal occurs. The stop signal may be used as a sampling signal to freeze the delaying of the start signal and trigger the time-to-digital conversion. The TDC output value may be output from the output port $Q_1$ to $Q_n$ that represent the time interval between the start and the stop signal.

Figure 14:
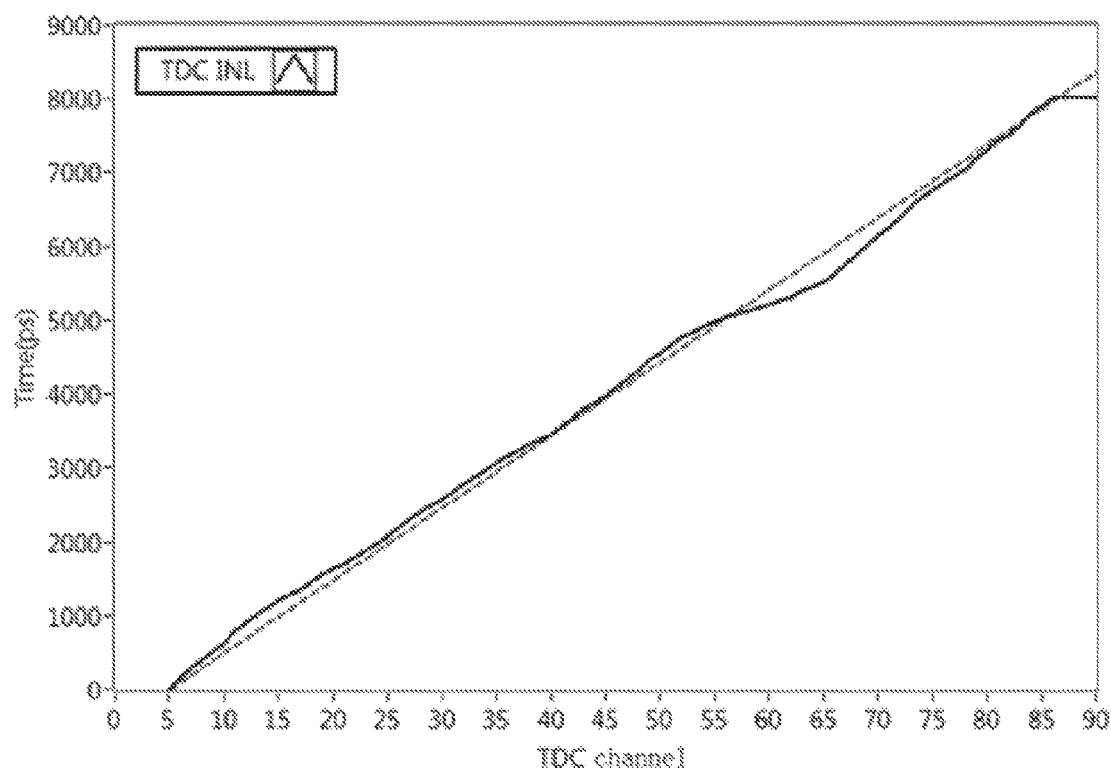
FIG. 14 is an example illustrating the time values corresponding to TDC channels according to some embodiments of the present disclosure.

FIG. 14 is an example illustrating the time values corresponding to TDC channels according to some embodiments of the present disclosure. As used herein, a TDC channel may correspond to an output port among $Q_1$ to $Q_n$, with a specific time and a time width. In an ideal circumstance, the delay time interval of the delay elements may be identical. The dash line may represent the time value corresponding to the TDC channels in such an ideal circumstance. However, due to the nonlinearity of the delay-line, the delay time interval of the delay elements may be non-identical. The solid line may represent the output time value corresponding to the TDC channels when the delay-line is not linear. The deviation of the solid line to the dash line may cause the deviation of the time information of the electrical pulse signal when it is converted into digital signal by the TDC. Thus, the TDC channels may need to be calibrated.

Figure 15:
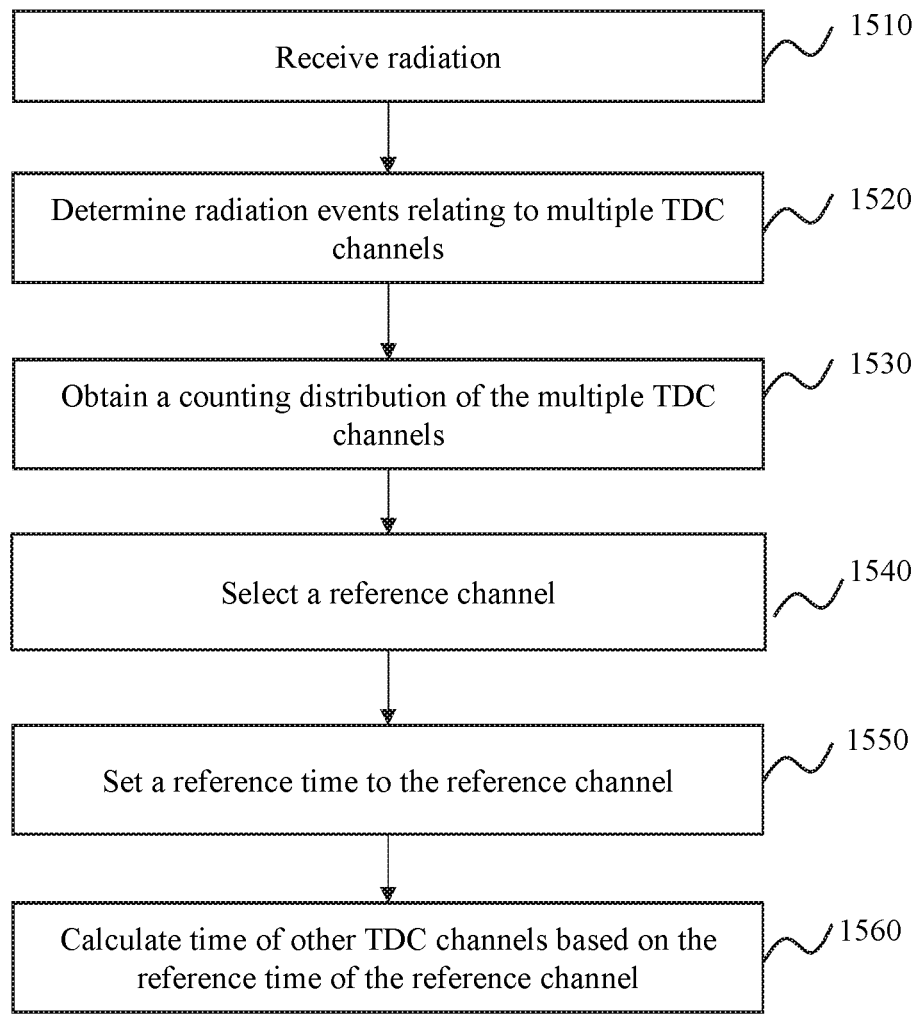
FIG. 15 is a flowchart illustrating a method to calibrate the output error of a TDC according to some embodiments of the present disclosure.

FIG. 15 is a flowchart illustrating a method to calibrate the output error of a TDC according to some embodiments of the present disclosure. Before the calibration process, the detector of the PET scanner may be initialized. The initialization may include resetting the parameters of the scanner and setting the time related value of the scanner to zero. Exemplary time related value of the scanner may include the operation time of the scanner, the processing time in the scanner, or the like, or a combination thereof. In step 1510, radiation may be received by the scintillator from the FOV of the PET scanner. In some embodiments, the radiation may be generated by a radiation source placed in the FOV.

In step 1520, radiation events relating to multiple TDC channels may be determined. Referring back to FIG. 8, the electrical pulse signal generated in response to one or more single events may be processed and sent to the TDC 804. The TDC 804 may convert the electrical pulse signal into a digital signal including the radiation event count, and output the radiation event count in the TDC channels. As used herein, a TDC channel may correspond to a time interval during which one or more radiation events may be detected. In some embodiments, when a TDC channel is determined, the output radiation event counts (or referred to as output counts for brevity) may be determined by counting the single events registered by the TDC channel within a specific time interval. The radiation event counts may be stored in a memory used for the TDC calibration and/or transferred to an external computing device for further processing. Under a certain condition, the counting may be stopped and the output counts of the TDC channels may be calculated separately in accordance with the serial number.

Figure 16:
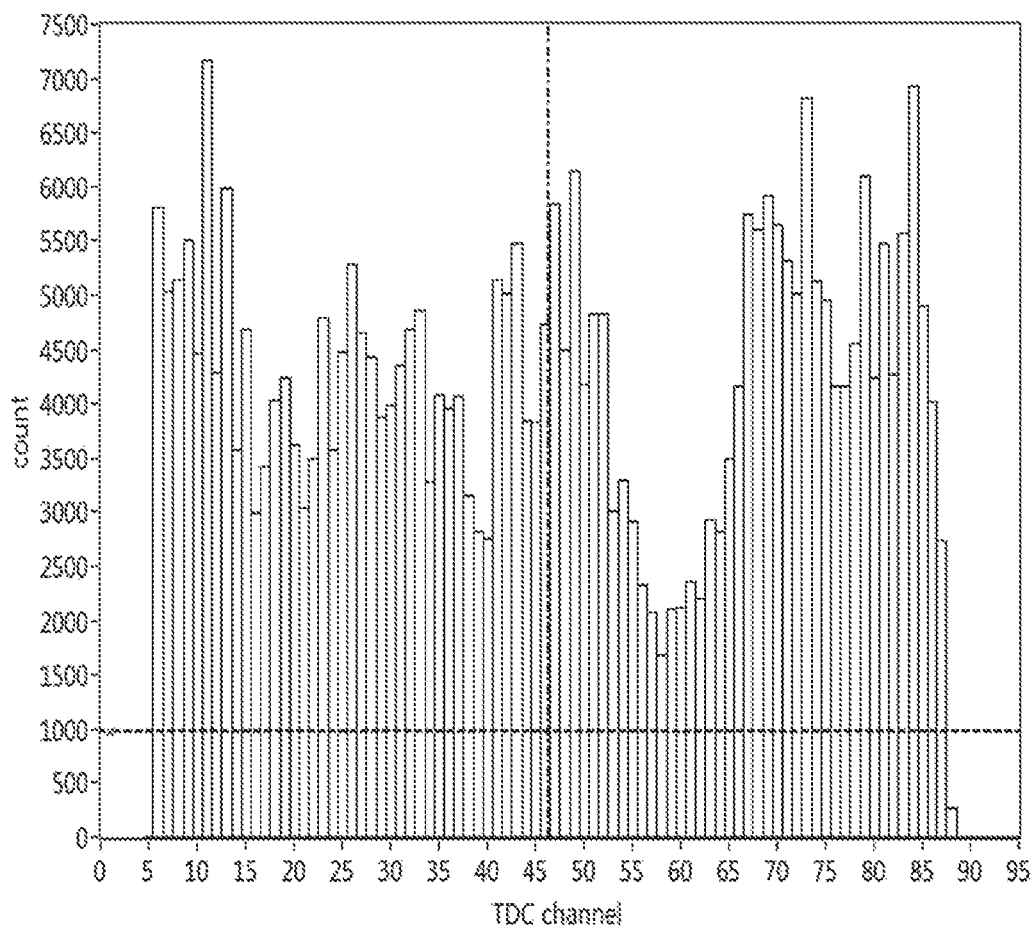
FIG. 16 is a column diagram illustrating an exemplary radiation event distribution in the TDC channels according to some embodiments of the present disclosure.

In step 1530, a counting distribution of the multiple TDC channels may be obtained according to the numbers of the output counts of the TDC channels. In some embodiments, the result of the counting distribution may be calculated after the output counts of the TDC channels are processed by a computing device. Alternatively, the result of the counting distribution may be described in a diagram or a table. In some embodiments, a column diagram may be used to illustrate the distribution. FIG. 16 is an exemplary radiation event distribution in the TDC channels using a column diagram according to some embodiments of the present disclosure. The horizontal-axis may represent the serial number of the TDC channels, and the vertical-axis may represent the radiation events output by corresponding TDC channels. In some embodiments, the output count of a TDC channel may be in proportion to the bandwidth of the TDC channel. The higher the column is as shown in FIG. 16, the broader the bandwidth of the channel may be, which may indicate that the corresponding delay time of the corresponding delay element is longer. In some embodiments, the bandwidth of a TDC channel may be the delay time interval of the corresponding delay element. The differences of the height of the columns may indicate that, in the TDC 804, the delay time of the delay elements thereof may be non-identical. In some embodiments, the counting may be stopped when the average number of output counts exceeds a predetermined value.

In step 1540, a reference channel may be selected. In some embodiments, the reference channel may be selected according to the counting distribution described by the column diagram. In some embodiments, the reference channel may divide the TDC channels into a first set and a second set. In some embodiments, the radiation event counts in the first set may equal to the radiation event counts in the second set. As an example, the first set may be the TDC channels located on one side of the reference channel, and the second set may be the TDC channels located on the other side of the reference channel. In FIG. 16, the vertical dash line may denote an exemplary reference channel (i.e., channel 46). The channels on the left side of the reference channel may be identified as the first set, and the channels on the right side of the reference channel may be identified as the second set. The sum of the height corresponding to the columns in the first set may equal to the sum of the height corresponding to the columns in the second set. In some embodiments, the reference channel may be set as the channel in the middle of the channels. The numbers of the TDC channels on the left side of the reference channel may equal to the numbers of the TDC channels on the right side of the reference channel. The horizontal dash line may denote the threshold to stop the counting of the output counts. For example, when the output counts of none of the TDC channels is lower than the threshold, the counting may be stopped.

In step 1550, a reference time may be set to the reference channel. In some embodiments, the time value output by the TDC channels may be a relative value. If the reference time of the reference channel is set, the time of the other channels may be calculated based on the reference time of the reference channel. In some embodiments, the reference time may be set as $$T_c = \frac{1}{2}T,$$

where T may denote the clock period of the TDC.

In step 1660, the time of the other TDC channels may be calculated based on the reference time. In some embodiments, the time of the other TDC channels may be calculated according to Equation (1) and Equation (2):

$$T_{i-1} = T_i - N_i \times \left(\frac{T}{\Sigma N_i}\right), i = c, c-1, c-2, c-3, \ldots, 0; \quad (1)$$

$$T_{i+1} = T_i + N_i \times \left(\frac{T}{\Sigma N_i}\right), i = c, c+1, c+2, c+3, \ldots; \quad (2)$$

where $T_i$ may represent the time value related to the ith TDC channel, c may represent a serial number of a TDC channel, $N_i$ may represent the output count of the ith TDC channel, and T may represent the clock period of the TDC. After the calculation, a mapping table between the time and the TDC channels may be established. The time of a radiation event may be determined according to the serial number of the output channel and the mapping table.

Figure 17:
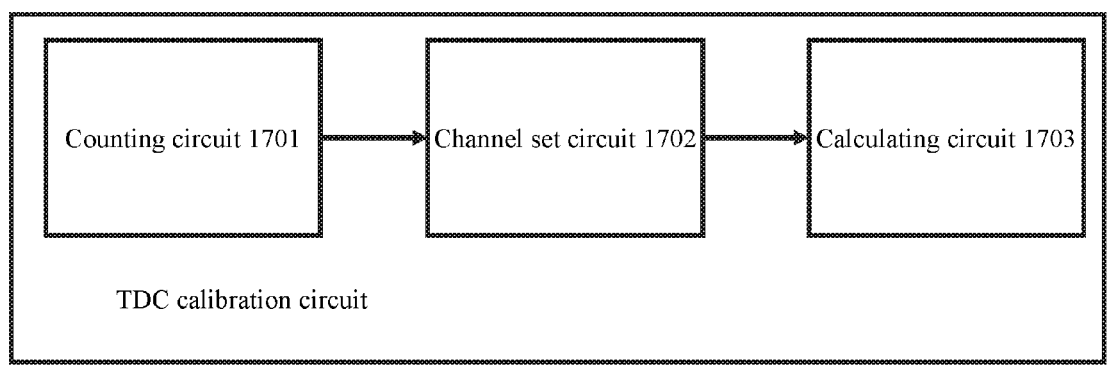
FIG. 17 is a block diagram illustrating a TDC calibration circuit according to some embodiments of the present disclosure.

FIG. 17 is a block diagram illustrating a TDC calibration circuit according to some embodiments of the present disclosure. The TDC calibration circuit 807 may include a counting circuit 1701, a channel set circuit 1702, and a calculating circuit 1703. The counting circuit 1701 may be configured to determine radiation event counts as described in step 1520 and step 1530 in FIG. 15. When detecting radiation events, the output time of a channel may be determined and the counting distribution of the multiple channels may be obtained by the counting circuit 1701. A reference channel may be selected by the channel set circuit 1702 as described in step 1640. In some embodiments, the TDC channels may be divided into different sets by the reference channel. The calculating circuit 1703 may be configured to set a reference time to the reference channel and further determine the time of the other TDC channels accordingly.

As will be also appreciated, the above described method embodiments may take the form of computer or controller implemented processes and apparatuses for practicing those processes. The disclosure can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A method for evaluating a working condition of a photodetector of a detector in an imaging device comprising:
receiving radiation by the detector in response to which a plurality of single events occur;
generating, by the photodetector, an electronic signal relating to the plurality of single events, wherein the electronic signal comprises time related information processed by a time-to-digital convertor (TDC) having multiple TDC channels;
determining a parameter of the electronic signal relating to the plurality of single events; and
evaluating the working condition of the photodetector based on the parameter and a threshold.

2. The method of claim 1, wherein the electronic signal comprises a pulse signal.

3. The method of claim 1 further comprising:
obtaining a distribution of the plurality of single events with respect to the multiple TDC channels;
selecting a reference channel from the multiple TDC channels;
dividing the multiple TDC channels into a first set of TDC channels and a second set of TDC channels based on the reference channel such that the number of single events of the first set is equal to the number of single events of the second set;
setting a reference time to the reference channel; and
calculating a time value relating to a characteristic TDC channel in the first set according to the reference time.

4. The method of claim 3, wherein the first set of TDC channels are on one side of the reference channel in a column diagram, and the second set of TDC channels are on the other side of the reference channel in the column diagram.

5. The method of claim 3, wherein the time value relating to the characteristic TDC channel is calculated based on the reference time, a serial number of the characteristic TDC channel, the single event count of the characteristic TDC channel, and a clock period of the TDC.

6. The method of claim 3, wherein the reference time is set as half of a clock period of the TDC.

7. The method of claim 1, wherein the parameter is a single event count or a characteristic of a photon energy spectrum of the radiation.

8. The method of claim 7 further comprising:
assigning the photodetector into a first set if the single event count exceeds the threshold.

9. The method of claim 7 further comprising:
determining the positon of a first peak of the photon energy spectrum;
determining the position of a characteristic peak corresponding to the first peak;
determining a deviation between the position of the first peak and the position of the characteristic peak; and
assigning the photodetector into a first set if the deviation is below the threshold.

10. A system, comprising:
a detector for receiving radiation in respond to which a plurality of single events occur;
a photodetector of the detector for generating an electronic signal relating to the plurality of single events; and
a processing module for determining a parameter of the electronic signal relating to the plurality of single events and evaluating the working condition of the photodetector based on the parameter and a threshold,
wherein the detector comprises a scintillator, and the radiation is generated by the background radiation of the scintillator.

11. The system of claim 10, the radiation received by the detector is generated by a radiation source placed in a field of view of the detector.

12. The system of claim 10, wherein the scintillator exhibits at least one characteristic radiation.

13. The system of claim 10, wherein the scintillator comprises a lutetium compound.

14. The system of claim 10, wherein the photodetector comprises at least one device selected from a group consisting of a photomultiplier, a silicon photomultiplier, and an avalanche diode.

15. The system of claim 10, wherein the photodetector is connected with a voltage divider.

* * * * *